(12) United States Patent
Fish et al.

(10) Patent No.: US 10,278,592 B2
(45) Date of Patent: May 7, 2019

(54) MODULAR SENSOR PLATFORM

(71) Applicant: Samsung Electronics Co., Ltd., Suwon-si (KR)

(72) Inventors: Ram Fish, San Jose, CA (US); James Schuessler, San Jose, CA (US); Julien Penders, Liege (BE); Lindsay Brown, Mierlo (NL); Frank Settemo Nuovo, Los Angeles, CA (US); Sheldon George Phillips, Glendale, CA (US); Tom Torfs, Kraainem (BE)

(73) Assignee: Samsung Electronics Co., Ltd. (KR)

( * ) Notice: Subject to any disclaimer, the term of this patent is extended or adjusted under 35 U.S.C. 154(b) by 373 days.

(21) Appl. No.: 14/286,620

(22) Filed: May 23, 2014

(65) Prior Publication Data

US 2015/0157220 A1 Jun. 11, 2015

Related U.S. Application Data

(63) Continuation-in-part of application No. 14/101,200, filed on Dec. 9, 2013, now Pat. No. 9,380,949.
(Continued)

(51) Int. Cl.
*A61B 5/1455* (2006.01)
*A61B 5/0205* (2006.01)
(Continued)

(52) U.S. Cl.
CPC ........ *A61B 5/02055* (2013.01); *A61B 5/0002* (2013.01); *A61B 5/14552* (2013.01);
(Continued)

(58) Field of Classification Search
None
See application file for complete search history.

(56) References Cited

U.S. PATENT DOCUMENTS 6,595,929 B2   7/2003   Stivoric et al.
6,619,835 B2   9/2003   Kita
(Continued)

FOREIGN PATENT DOCUMENTS

CN   101330869 A   12/2008
CN   101484065     7/2009
(Continued)

OTHER PUBLICATIONS

Notification of Transmittal of the International Search Report and the Written Opinion of the International Searching Authority, or the Declaration corresponding to International Application No. PCT/IB2015/001979, dated Mar. 3, 2016.
(Continued)

*Primary Examiner* — Eric Winakur
*Assistant Examiner* — Marjan Fardanesh
(74) *Attorney, Agent, or Firm* — McAndrews, Held & Malloy, Ltd.

(57) ABSTRACT

Exemplary embodiments for reconfiguring a storage system comprise a modular sensor platform, comprising: a base module comprising, a display, a processor, a memory and a communication interface; a band removably coupled to the base module such that the band is replaceable with different types of bands; and a sensor module that collects data from a user, the sensor module in communication with the base module and removably coupled to the band such that the sensor module is replaceable with different types of sensor modules, the sensor module further comprising a plurality of sensor units that are removably coupled to the sensor module such that individual sensor units are replaceable with different types of sensor units.

23 Claims, 9 Drawing Sheets

Related U.S. Application Data

(60) Provisional application No. 61/984,694, filed on Apr. 25, 2014.

(51) Int. Cl.
    *A61B 5/00*               (2006.01)
    *A61B 5/0402*           (2006.01)
    *A61B 5/11*              (2006.01)
    *A61B 5/01*              (2006.01)
    *A61B 5/053*            (2006.01)
    *A61B 5/021*            (2006.01)

(52) U.S. Cl.
    CPC ............... *A61B 5/681* (2013.01); *A61B 5/01* (2013.01); *A61B 5/02141* (2013.01); *A61B 5/0402* (2013.01); *A61B 5/0533* (2013.01); *A61B 5/1118* (2013.01); *A61B 5/7278* (2013.01); *A61B 2560/0242* (2013.01); *A61B 2560/045* (2013.01)

(56) References Cited

U.S. PATENT DOCUMENTS

| | | |
|---|---|---|
| 7,127,432 B2 | 10/2006 | Rubin et al. |
| 7,470,235 B2 | 12/2008 | Moriya et al. |
| 7,512,985 B1 | 3/2009 | Grabarnik et al. |
| 7,618,260 B2 | 11/2009 | Daniel |
| 7,894,888 B2 | 2/2011 | Chan et al. |
| 8,140,143 B2 | 3/2012 | Picard et al. |
| 8,142,357 B2 | 3/2012 | Suyama et al. |
| 8,251,903 B2 | 8/2012 | LeBoeuf |
| 8,280,469 B2 * | 10/2012 | Baker, Jr. ............ A61B 5/14551 600/310 |
| 8,504,145 B2 | 8/2013 | Kuroda et al. |
| 8,618,930 B2 | 12/2013 | Papadopoulos |
| 8,768,424 B2 | 1/2014 | Crowe et al. |
| 8,647,268 B2 | 2/2014 | Tran |
| 8,965,498 B2 | 2/2015 | Katra et al. |
| 2003/0212336 A1 | 11/2003 | Lee et al. |
| 2005/0234351 A1 | 10/2005 | Nishii et al. |
| 2007/0040449 A1 | 2/2007 | Spurlin et al. |
| 2007/0279852 A1 | 12/2007 | Daniel et al. |
| 2008/0171945 A1 | 7/2008 | Dotter |
| 2008/0294058 A1 | 11/2008 | Shklarski |
| 2009/0018409 A1 | 1/2009 | Banet |
| 2009/0048526 A1 | 2/2009 | Aarts et al. |
| 2009/0163820 A1 | 6/2009 | Eerden |
| 2009/0270743 A1 | 10/2009 | Dugan et al. |
| 2009/0306485 A1 | 12/2009 | Bell |
| 2009/0322513 A1 | 12/2009 | Hwang et al. |
| 2010/0076331 A1 | 3/2010 | Chan et al. |
| 2010/0210956 A1 | 8/2010 | Im |
| 2010/0267361 A1 | 10/2010 | Sullivan |
| 2010/0268056 A1 * | 10/2010 | Picard .................. A61B 5/0531 600/388 |
| 2010/0306854 A1 | 12/2010 | Neergaard |
| 2011/0213255 A1 | 9/2011 | Finburgh |
| 2011/0234160 A1 | 9/2011 | Smith |
| 2011/0245630 A1 | 10/2011 | St Pierre |
| 2011/0288382 A1 | 11/2011 | Finburgh |
| 2012/0030165 A1 | 2/2012 | Guirguis |
| 2012/0045303 A1 | 2/2012 | Murray |
| 2012/0059233 A1 | 3/2012 | Huber |
| 2012/0065514 A1 | 3/2012 | Naghavi et al. |
| 2012/0071731 A1 | 3/2012 | Gottesman |
| 2012/0082014 A1 | 4/2012 | Lai |
| 2012/0203076 A1 | 8/2012 | Fatta et al. |
| 2013/0014706 A1 | 1/2013 | Menkes |
| 2013/0261405 A1 | 3/2013 | Lee et al. |
| 2013/0141235 A1 | 6/2013 | Utter, II |
| 2013/0165817 A1 | 6/2013 | Horst |
| 2013/0192050 A1 | 8/2013 | LeMieux |
| 2013/0211204 A1 | 8/2013 | Caduff et al. |
| 2013/0282679 A1 | 10/2013 | Khin |
| 2013/0317333 A1 | 11/2013 | Yang |
| 2013/0318347 A1 | 11/2013 | Moffat |
| 2013/0324072 A1 | 12/2013 | Fish et al. |
| 2014/0142403 A1 | 5/2014 | Brumback et al. |
| 2014/0159640 A1 | 6/2014 | Yoshikawa et al. |
| 2014/0343383 A1 | 11/2014 | Sato |
| 2015/0164404 A1 | 6/2015 | Euliano et al. |

FOREIGN PATENT DOCUMENTS

| | | |
|---|---|---|
| CN | 101950153 A | 1/2011 |
| EP | 00330434 A1 | 8/1989 |
| EP | 1965697 A2 | 10/2008 |
| JP | H07116141 A | 5/1995 |
| JP | 2005324004 A | 11/2005 |
| JP | 2006271896 A | 10/2006 |
| JP | 2008119197 A | 5/2008 |
| JP | 2009-519737 A | 5/2009 |
| JP | 2010004972 A | 1/2010 |
| JP | 2013063205 A | 4/2013 |
| JP | 2013-094482 A | 5/2013 |
| JP | 2013-121420 A | 6/2013 |
| KR | 10-1038432 B1 | 1/2011 |
| KR | 10-2011-0012784 A | 9/2011 |
| KR | 10-2012-0033526 A | 4/2012 |
| KR | 2013 0024468 A | 3/2013 |
| KR | 20130024468 A | 3/2013 |
| KR | 10-2013-0111713 A | 11/2013 |
| RU | 2008-129670 A | 1/2010 |
| WO | 90-00366 A1 | 1/1990 |
| WO | 2004107971 A2 | 12/2004 |
| WO | 2006-018833 A2 | 2/2006 |
| WO | 2006-018833 A3 | 3/2006 |
| WO | 2007-072239 A2 | 6/2007 |
| WO | 2007-072239 A3 | 10/2007 |
| WO | 2009125349 | 10/2009 |
| WO | 2010/120945 A1 | 10/2010 |
| WO | 2010120945 A1 | 10/2010 |
| WO | 2010135516 | 11/2010 |
| WO | 2011/109716 A2 | 9/2011 |
| WO | 2013/175314 A2 | 11/2013 |
| WO | 2013175314 A2 | 11/2013 |
| WO | 2014120945 A1 | 8/2014 |

OTHER PUBLICATIONS

International Search Report corresponding to International Application No. PCT/IB2015/001979, dated Mar. 3, 2016.
Written Opinion of the International Searching Authority, or the Declaration corresponding to International Application No. PCT/IB2015/001979, dated Mar. 3, 2016.
"Blocks modular smartwatch: Like Project Ara for your wrist," W.Shanklin, Gizmag, Mar. 6, 2014.
"A Survey on Wearable Sensor-Based Systems for Health Monitoring and Prognosis," A. Pantelopoulos and N.G. Bourbakis, IEEE Transactions on Systems, Man and Cybernetics, vol. 40, No. 1, Jan. 2010.
"Multisensor Fusion in Smartphones for Lifestyle Monitoring," R.K. Ganti, S. Srinivasan, and A. Gacic, International Conference on Body Sensor Networks, 2010.
"A 5.2mW Self-Configured Wearable Body Sensor Network Controller and a 12uW Wireless Powered Sensor for a Continuous Health Monitoring System," J.Yoo, L.Yan, S.Lee, Y.Kim, and H-J Yoo, IEEE Journal of Solid-state Circuits, vol. 45, No. 1, Jan. 2010.
Mare et al., Hide-n-sense: preserving privacy efficiently in wireless mhealth, Mobile Networks and Applications 19.3 (Jun. 2014): 331-344. DOI: http://dx.doi.org/10.1007/s11036-013-0447-x ProQuest document ID: 1540736834 Jun. 1, 2014.
European Patent Office, Communication with extended European search report in Application No. 14196858.6, dated Jun. 25, 2015 (11 pages).
Notification of Transmittal of the International Search Report and the Written Opinion of the International Searching Authority, or the Declaration corresponding to International Application No. PCT/IB2015/001559, dated Jan. 20, 2016.

(56) References Cited

OTHER PUBLICATIONS

International Search Report corresponding to International Application No. PCT/IB2015/001559, dated Jan. 20, 2016.
Written Opinion of the International Searching Authority, or the Declaration corresponding to International Application No. PCT/IB2015/001559, dated Jan. 20, 2016.
Communication with European Examination Report corresponding to European Application No. 14196858.6, dated Oct. 6, 2016.
Notification of Transmittal of the International Search Report and Written Opinion of the International Searching Authority Authority, or the Declaration corresponding to International Patent Application No. PCT/IB2014/003257, dated Jan. 11, 2016.
International Search Report corresponding to International Patent Application No. PCT/IB2014/003257, dated Jan. 11, 2016.
Written Opinion of the International Searching Authority corresponding to International Patent Application No. PCT/IB2014/003257, dated Jan. 11, 2016.
Notification of Transmittal of the International Search Report and the Written Opinion of the International Searching Authority, or the Declaration corresponding to International Application No. PCT/IB2015/001997, dated Mar. 3, 2016.
International Search Report corresponding to International Application No. PCT/IB2015/001997, dated Mar. 3, 2016.
Written Opinion of the International Searching Authority, or the Declaration corresponding to International Application No. PCT/IB2015/001997, dated Mar. 3, 2016.
Notification Concerning Transmittal of International Preliminary Report on Patentability dated Apr. 20, 2017 with International Preliminary Report on Patentability corresponding to PCT/IB2015/001997.
Examination Report dated Jun. 9, 2017 corresponding to EP Application No. 14196858.6.
International Search Report corresponding to International Patent Application No. PCT/IB2014/003245, dated Jul. 29, 2015.
Notification of Transmittal of The International Search Report and the Written Opinion of the International Searching Authority, or the Declaration corresponding to International Patent Application No. PCT/IB2014/003245, dated Jul. 29, 2015.
Written Opinion of the International Searching Authority corresponding to International Patent Application No. PCT/IB2014/003245, dated Jul. 29, 2015.
Notification Concerning Transmittal of International Preliminary Report on Patentability with International Preliminary Report on Patentability corresponding to PCT/IB2015/001559, dated Dec. 8, 2016 and Written Opinion of the International Searching Authority dated Jan. 20, 2016.
Examination Report dated Oct. 8, 2018 from the Taiwan Patent Office in respect of the Taiwan Patent Application No. 103142521.
Examination report (NOA) dated Nov. 13, 2018 from the Japanese Patent Office in respect of the Japanese Patent Application No. 2014-248624.
Second Office Action dated Feb. 19, 2019 from the China Patent Office in respect of the China Patent Application No. 201410748459.X.

* cited by examiner

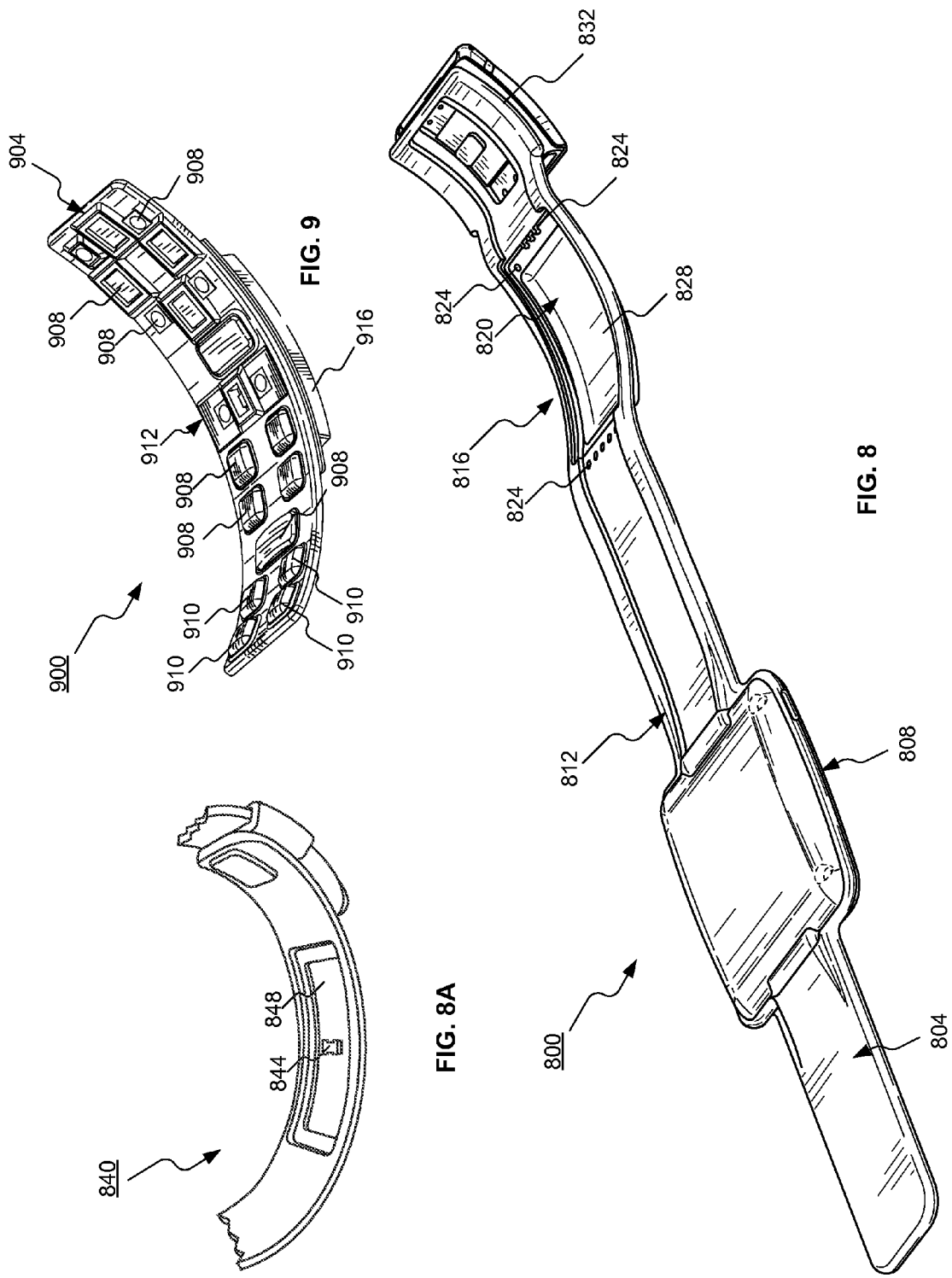

MODULAR SENSOR PLATFORM

RELATED APPLICATIONS

The present application is a continuation-in-part application of, and claims priority to U.S. application Ser. No. 14/101,200, filed Dec. 9, 2013, and also claims priority to U.S. Provisional Application No. 61/984,694, filed Apr. 25, 2014, all of which are incorporated herein by reference in their entirety.

BACKGROUND

The invention relates to modular sensor platform, and more particularly, to a modular sensor platform in a device wearable on a wrist of an individual.

Wearable devices are becoming increasingly popular. For example, wearable devices equipped with sensors are known that may track user data such as activity data (duration, step count, calories burned), sleep statistics, and/or physiological data (e.g., heart rate, perspiration and skin temperature). Typically, sensor-equipped wearable devices are implemented as bands or watches that may be worn on the user's wrist.

However, conventional wearable sensor devices require the user discard or replace the entire device due to a loss of function, even if the loss is caused by a relatively minor component, such as a sensor that becomes worn out due to normal wear. Users also often replace the device when a new device with new or different tracking functions becomes available.

Accordingly, what is needed is an improved architecture for wearable sensor devices that can accommodate both replacement and addition of sensor functionality.

BRIEF SUMMARY

Certain embodiments of the present invention provide a portable power source for charging an electronic device wearable over a wrist of a user.

The exemplary embodiment provides a modular sensor platform. Aspects of exemplary embodiment include a base module comprising, a display, a processor, a memory and a communication interface; a band removably coupled to the base module such that the band is replaceable with different types of bands; and a sensor module that collects data from a user, the sensor module in communication with the base module and removably coupled to the band such that the sensor module is replaceable with different types of sensor modules, the sensor module further comprising a plurality of sensor units that are removably coupled to the sensor module such that individual sensor units are replaceable with different types of sensor units.

According to the method and system disclosed herein, the exemplary embodiments provide a platform whereby a plurality of different sensor modules may be sold and manufactured by different entities. These entities may make different types of sensor modules for different use cases. The modular sensor platform of the exemplary embodiments therefore enables different types of base modules, bands, and sensor units to be manufactured and sold separately. The result is that users may be allowed to mix and match different combinations of base modules, sensor modules, bands and sensor units to suit their needs.

In one embodiment, the invention provides a device for measuring data indicative of a physiological activity of a user and is wearable on a body part of the user. The system includes a band that can be fitted over the body part, and has an interior surface contacting the body part when worn by the user. The device also includes a modular sensing circuitry that is removably disposed on the interior surface, and can be in contact with the body part. The system also includes a plurality of multi-spectral light sources disposed on the interior surface adjacent the modular sensing circuitry to emit multi-spectral lights onto the body part. The modular sensing circuitry receives data indicative of a photoplethysmogram (PPG) signal of the user.

In another embodiment, the invention provides a device for measuring a physiological activity of a user and is wearable on a body part of the user. The device includes a band that can be fitted over the body part. The band has an interior surface contacting the body part when worn by the user. The device also includes modular sensing circuitry that is removably disposed on the interior surface. The modular sensing circuitry can also be configurable to contact the body part. The device also includes a sensor on the exterior surface to receive data indicative of an electrocardiogram (ECG) signal of the user with the modular sensing circuitry. The device also includes a plurality of light sources on the interior surface adjacent the modular sensing circuitry to emit lights onto the body part. The modular sensing circuitry receives data indicative of a photoplethysmography (PPG) signal of the user. The device includes a processor disposed on the band to derive data indicative of blood pressure of the user from the ECG signal and the PPG signal.

In yet another embodiment, the invention provides a device for measuring a physiological activity of a user that is wearable on a body part of a user. The device includes a band that is configurable to be fitted over the wrist. The band has an interior surface contacting the body part when worn by the user. The device also includes modular sensing circuitry that is removably disposed on the interior surface to measure the physiological activity of the user. The modular sensing circuitry includes a plurality of individual sensors to measure the physiological activity. The plurality of individual sensors are generally contoured to the shape of the body part.

In yet another embodiment, the invention provides a system for measuring a physiological activity of a user that is wearable on a body part of a user. The system includes a band that is configurable to be fitted over the body part. The band also has an interior surface contacting the body part when worn by the user. The system includes an interface disposed in the interior surface, and a plurality of sensor modules. Each of the sensor modules receives data indicative of a physiological activity of the user, and is removably disposed on the interior surface, and detachably engagable with the interface.

BRIEF DESCRIPTION OF SEVERAL VIEWS OF THE DRAWINGS

The features and utilities described in the foregoing brief summary, as well as the following detailed description of certain embodiments of the present general inventive concept below, will be better understood when read in conjunction with the accompanying drawings of which:

FIG. 8 illustrates an exemplary modular sensing circuitry in accordance with embodiments of the present invention.

FIG. 8A illustrates an interface receptacle showing an exemplary interface in accordance with embodiments of the present invention.

FIG. 9 illustrates an exemplary complementary metal-oxide-semiconductor ("CMOS") sensor module in accordance with embodiments of the present invention.

Figure 1:
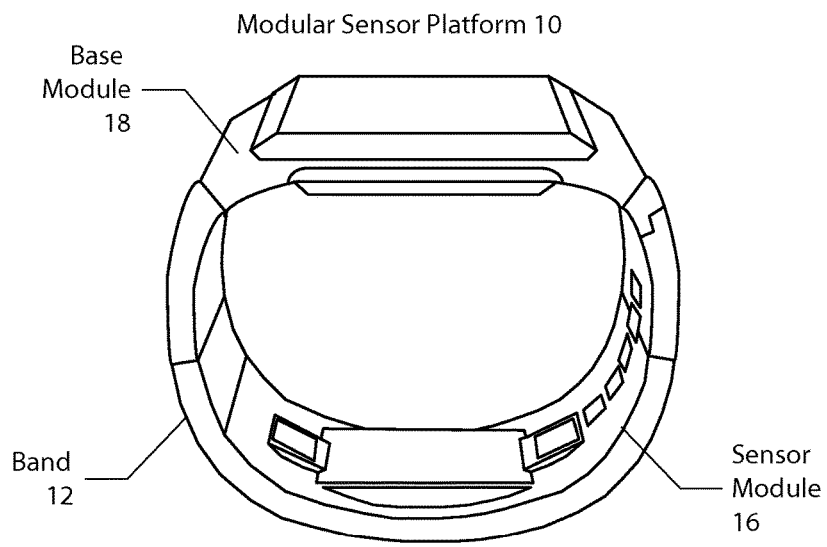
FIGS. 1 and 2 are block diagrams illustrating exemplary embodiments of a modular sensor platform.

For the purpose of illustrating the general inventive concept of the invention, certain embodiments are shown in the drawings. It should be understood, however, that the present invention is not limited to the arrangements and instrumentality shown in the attached drawings.

DETAILED DESCRIPTION

Reference will now be made in detail to the embodiments of the present general inventive concept, examples of which are illustrated in the accompanying drawings, wherein like reference numerals refer to the like elements throughout. The embodiments are described below in order to explain the present general inventive concept while referring to the figures.

Before any embodiments of the invention are explained in detail, it is to be understood that the invention is not limited in its application to the details of construction and the arrangement of components set forth in the following description or illustrated in the drawings.

Advantages and features of the present invention and methods of accomplishing the same may be understood more readily by reference to the following detailed description and the drawings. The present general inventive concept may, however, be embodied in many different forms of being practiced or of being carried out in various ways and should not be construed as being limited to the embodiments set forth herein. Rather, these embodiments are provided so that this disclosure will be thorough and complete and will fully convey the general inventive concept to those skilled in the art, and the present general inventive concept is defined by the appended claims. In the drawings, the thickness of layers and regions are exaggerated for visual clarity.

Also, the phraseology and terminology used in this document are for the purpose of description and should not be regarded as limiting. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

As should also be apparent to one of ordinary skill in the art, the systems shown in the figures are models of what actual systems might be like. Some of the modules and logical structures described are capable of being implemented in software executed by a microprocessor or a similar device, or of being implemented in hardware using a variety of components including, for example, application specific integrated circuits ("ASICs"). A term like "processor" may include or refer to both hardware and/or software. No specific meaning is implied or should be inferred simply due to the use of capitalization.

Likewise, the term "component" or "module", as used herein, means, but is not limited to, a software or hardware component, such as a field programmable gate array (FPGA) or ASIC, which performs certain tasks. A component or module may advantageously be configured to reside in the addressable storage medium and configured to execute on one or more processors. Thus, a component or module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for the components and components or modules may be combined into fewer components and components or modules or further separated into additional components and components or modules.

Unless defined otherwise, all technical and scientific terms used herein have the same meaning as commonly understood by one of ordinary skill in the art to which this invention belongs. Further, unless defined otherwise, all terms defined in generally used dictionaries should have their ordinary meaning. It is noted that the use of any and all examples, or exemplary terms provided herein is intended merely to better illuminate the general inventive concept and is not a limitation on the scope of the invention unless otherwise specified.

Exemplary embodiments provide a modular sensor platform. Aspects of exemplary embodiment include a base module comprising, a display, a processor, a memory and a communication interface; a band removably coupled to the base module such that the band is replaceable with different types of bands; and a sensor module that collects data from a user. In one embodiment, the sensor module may be removably coupled to the band such that the sensor module is replaceable with different types of sensor modules. In another embodiment, the sensor module comprises a plurality of sensor units that may be removably coupled to the sensor module such that individual sensor units are replaceable with different types of sensor units.

According to the method and system disclosed herein, a modular sensor platform is provided that enables different types of base modules, bands, and sensor units to be manufactured and sold separately by different entities for different use cases. The result is that users may be allowed to mix and match different combinations of base modules, sensor modules, bands and sensor units to suit their needs. Furthermore, developers or researchers in fields related to physiological sensing benefit by focusing development on the sensor itself and utilizing a standard support platform that supplies power, computation and communication in a known configuration.

Embodiments of the invention relate to a system for measuring data indicative of a physiological activity of a user.

Figure 2:
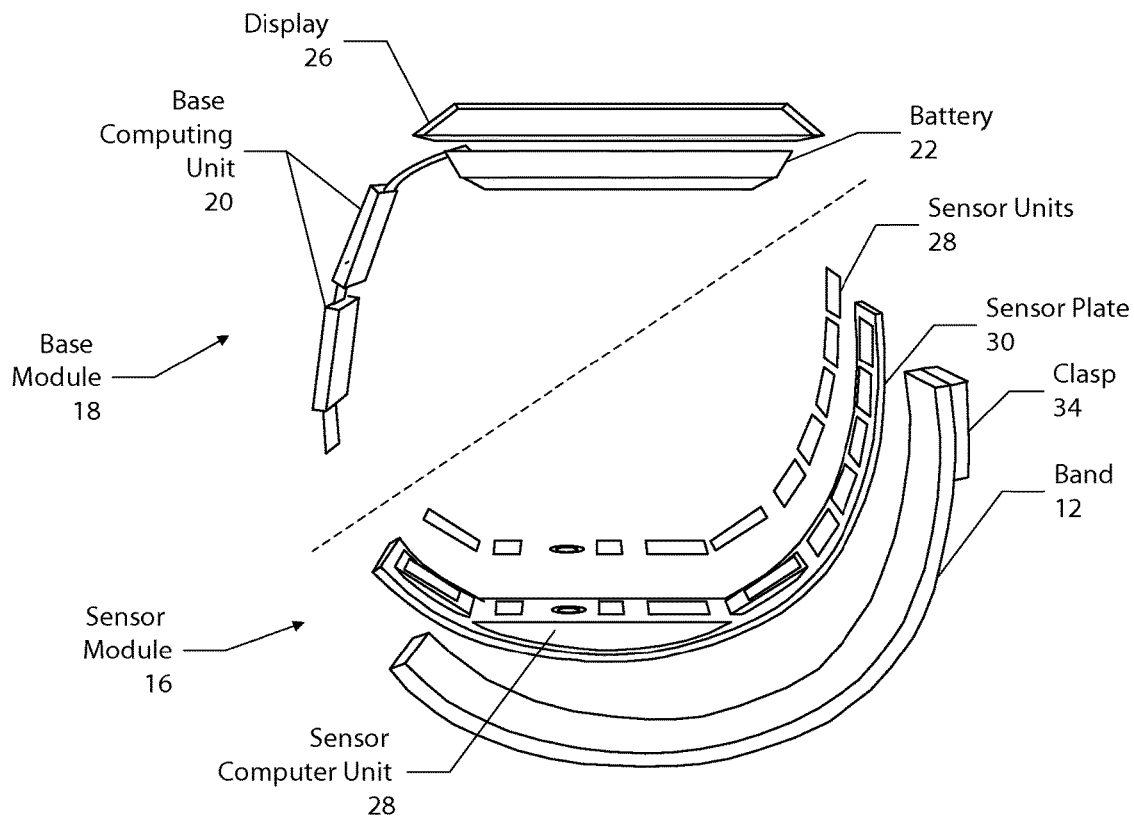

FIGS. 1 and 2 are block diagrams illustrating exemplary embodiments of a modular sensor platform. The modular sensor platform 10 may include a base module 18, a band 12, and a sensor module 16 coupled to the band 12.

In the embodiment shown in FIG. 1, the modular sensor platform 10 may be implemented as a wearable sensor device, such as a smart watch that fits on a user's wrist. The sensor module 16 may be positioned within the band 12, such that the sensor module 16 is located at the bottom of the user's wrist in contact with the user's skin to collect physiological data from the user. The base module 18 attaches to the band 12 such that the base module 18 is positioned on top of the wrist and performs functions such as displaying time, performing calculations and displaying data including sensor data collected from the sensor module 16. In one embodiment, the band 12 may be integrated with the base module 18. In another embodiment, the band 12 may be integrated with the sensor module 16. In a further embodiment, the band 12 may be separate from both the base module 18 and the sensor module 16.

In the embodiment shown in FIG. 2, the base module 18 may comprise a display 26 and a base computing unit 20. As will be discussed more fully with respect to FIG. 2, the base computing unit 20 may include a processor, memory, a communication interface and a set of sensors, such as an accelerometer and thermometer, for instance.

The modular sensor platform 10 enables components of the platform to be easily exchanged with different types of components. For example, in one embodiment, the band 12 may be removably coupled to the base module 18 so that the band 12 is replaceable with a different type of band (e.g., different size, different shape, and/or different materials). Replacement bands may be made by the same or different entities of original band 12. In one embodiment, the band 12 may include a hollow portion for insertion of the base computing unit 20 of the base module 18.

In a further embodiment, the sensor module 16 collects physiological, activity data, and/or sleep statistics from a user and is in communication with the base module 18. The sensor module 16 may be removably coupled to the band 12 such that the sensor module 16 is replaceable with different types of sensor modules.

In one embodiment, the sensor module 16 may further comprise a plurality of sensor units 28 that are removably coupled to the sensor module 16 such that at least a portion of individual sensor units 28 are replaceable with different types of sensor units.

In one embodiment, the sensor units 28 may be housed on a sensor plate 30. According to one embodiment, the sensor plate 30 may be removably coupled to the band 12, such that the sensor plate 30 and all the sensor units 28 thereon may be replaced with a different type of sensor plate 30. For example, the sensor plate 30 may be replaced with a different sized sensor plate 30 to accommodate a different sized wrist. In one embodiment, replacement sensor plates 30 may be provided by the same or a different entity than the original sensor plate 30.

According to one aspect of the exemplary embodiment, at least portion of the sensor units 28 may be further removably coupled to the sensor plate 30 so that the sensor units 28 may be individually replaced with new or different types of sensor units. For example, with electrode-type sensors, the electrodes may wear out over time. Rather than having to buy an entire new smart watch, the user may simply replace worn-out sensor units 28 with new ones by inserting new sensor units 28 into the existing sensor plate 30.

In another embodiment, the sensor plate 30 may be removed from the band 12 so that the existing sensor plate 30 may be used with a different type of band 12. For example, the sensor plate 30 may be removed from a plastic band 12 that is worn during the day and inserted into a felt band that may be worn during sleep. In yet another embodiment, the sensor plate 30 may be removed from the band 12 and replaced with a sensor plate 30 having different types of sensor units 28, including different sized sensor units 28 or sensor units 28 that are spaced differently on the sensor plate 30.

In one embodiment, the sensor plate 30 may be affixed to the band 12 using any number of know mechanisms. For example, in one embodiment, the sensor plate 30 may be affixed to the band 12 via a snap mechanism (e.g., tabs, slots, magnets and the like). In an alternative embodiment, the sensor plate 30 may be affixed to the band 12 via screws.

As shown in FIG. 2, in one embodiment, the modular sensor platform 10 further includes at least one battery 22. In one embodiment, the battery 22 may be housed within the base module 18. In another embodiment, the battery 22 may be housed within the band 12.

Accordingly, a plurality of different sensor modules may be sold and manufactured by different entities. That is, different entities may make different types of sensor modules for different use cases. The modular sensor platform of the exemplary embodiments therefore enable different types of base modules, bands, sensor plates and sensor units to be manufactured and sold separately. Consequently, a modular sensor platform is provided that enables users to mix and match different combinations of base modules, sensor modules, bands and sensor units to suit their needs.

According to a further aspect of the exemplary embodiment, a user may wear one base module 18 that wirelessly communicates with multiple sensor modules 16 worn on different body parts of the user to form a body area network. Data collected by each of the sensor modules 16 could be bursts to the base module 18 periodically for storage and/or analysis when the base module 18 is in an active mode. Transferring the sensor data only periodically allows the base module 18 to be placed in sleep mode more often to save power. Alternatively, the data could be continually streamed from the sensor modules 16 to the base module 18 if the base module 18 remains in active mode.

In the embodiment shown in FIG. 1, the wearable sensor platform 10 may be implemented as a smart watch or other wearable device that fits on part of a body, here a user's wrist.

The wearable sensor platform 10 may also include a clasp 34 coupled to the band 12. In some embodiments, the modules and/or components of the wearable sensor platform 10 may be removable by an end user (e.g., a consumer, a patient, a doctor, etc.). However, in other embodiments, the modules and/or components of the wearable sensor platform 10 are integrated into the wearable sensor platform 10 by the manufacturer and may not be intended to be removed by the end user. The wearable sensor platform 10 may be waterproof or water sealed.

The band or strap 12 may be one piece or modular. The band 12 may be made of a fabric. For example, a wide range of twistable and expandable elastic mesh/textiles are contemplated. The band 12 may also be configured as a multi-band or in modular links. The band 12 may include a latch or a clasp mechanism to retain the watch in place in certain implementations. In certain embodiments, the band 12 will contain wiring (not shown) connecting, among other things, the base module 18 and sensor module 16. Wireless communication, alone or in combination with wiring, between base module 18 and sensor module 16 is also contemplated.

The sensor module 16 may be removably attached on the band 12, such that the sensor module 16 is located at the bottom of the wearable sensor platform 10 or, said another way, on the opposite end of the base module 18. Positioning the sensor module 16 in such a way to place it in at least partial contact with the skin on the underside of the user's wrist to allow the sensor units 28 to sense physiological data from the user. The contacting surface(s) of the sensor units 28 may be positioned above, at or below, or some combination such positioning, the surface of the sensor module 16.

The base module 18 attaches to the band 12 such that the base module 18 is positioned at top of the wearable sensor platform 10. Positioning the base module 18 in such a way to place it in at least partial contact with the top side of the wrist.

The base module 18 may include a base computing unit 20 and a display 26 on which a graphical user interface (GUI) may be provided. The base module 18 performs functions including, for example, displaying time, performing calculations and/or displaying data, including sensor data collected from the sensor module 16. In addition to communication with the sensor module 16, the base module 18 may wirelessly communicate with other sensor module(s) (not shown) worn on different body parts of the user to form a body area network, or with other wirelessly accessible devices (not shown), like a smartphone, tablet, display or other computing device. As will be discussed more fully below with respect to FIG. 3, the base computing unit 20 may include a processor 36, memory 38, input/output 40, a communication interface 42, a battery 22 and a set of sensors 44, such as an accelerometer/gyroscope 46 and thermometer 48. In other embodiments, the base module 18 can also have other sizes, cases, and/or form factors, such as, for example, oversized, in-line, round, rectangular, square, oval, Carre, Garage, Tonneau, asymmetrical, and the like.

The sensor module 16 collects data (e.g., physiological, activity data, sleep statistics and/or other data), from a user and is in communication with the base module 18. The sensor module 16 includes sensor units 28 housed in a sensor plate 30. For certain implementations, because a portable device, such as a wristwatch, has a very small volume and limited battery power, sensor units 28 of the type disclosed may be particularly suited for implementation of a sensor measurement in a wristwatch. In some embodiments, the sensor module 16 is adjustably attached to the band 12 such that the base module 18 is not fixedly positioned, but can be configured differently depending on the physiological makeup of the wrist.

The sensor units 28 may include an optical sensor array, a thermometer, a galvanic skin response (GSR) sensor array, a bioimpedance (BioZ) sensor array, an electrocardiogram (ECG) sensor, or any combination thereof. The sensors units 28 may take information about the outside world and supply it to the wearable modular sensor platform 10. The sensors 28 can also function with other components to provide user or environmental input and feedback to a user. For example, a MEMS accelerometer may be used to measure information such as position, motion, tilt, shock, and vibration for use by processor 36. Other sensor(s) may also be employed. The sensor module 16 may also include a sensor computing unit 32. The sensor units 28 may also include biological sensors (e.g., pulse, pulse oximetry, body temperature, blood pressure, body fat, etc.), proximity detector for detecting the proximity of objects, and environmental sensors (e.g., temperature, humidity, ambient light, pressure, altitude, compass, etc.).

In other embodiments, the clasp 34 also provides an ECG electrode. One or more sensor units 28 and the ECG electrode on the clasp 34 can form a complete ECG signal circuit when the clasp 34 is touched. The sensor computing unit 32 may analyze data, perform operations (e.g., calculations) on the data, communicate data and, in some embodiments, may store the data collected by the sensor units 28. In some embodiments, the sensor computing unit 32 receives (for example, data indicative of an ECG signal) from one or more of the sensors of the sensor units 28, and processes the received data to form a predefined representation of a signal (for example, an ECG signal).

The sensor computing unit 32 can also be configured to communicate the data and/or a processed form of the received data to one or more predefined recipients, for example, the base computing unit 20, for further processing, display, communication, and the like. For example, in certain implementations the base computing unit 20 and/or sensor computing unit determine whether data is reliable and determine an indication of confidence in the data to the user.

In some embodiments, the sensor computing unit 32 may be integrated into the sensor plate 30. In other embodiments, the sensor computing unit 32 may be omitted or located elsewhere on the wearable sensor platform 10 or remotely from the wearable sensor platform 10. In an embodiment where the sensor computing unit 32 may be omitted, the base computing unit 20 may perform functions that would otherwise be performed by the sensor computing unit 32. Through the combination of the sensor module 16 and base module 18, data may be collected, transmitted, stored, analyzed, transmitted and presented to a user.

In some embodiments, the clasp 34 is disposed closer to the display/GUI 26. Similarly, in FIG. 2, the battery 22 is housed with the base module 18. In the embodiment shown in FIG. 1, the battery 22 is housed on the band 12, opposite to the display 26. However, it should be understood that, in some embodiments, the battery 22 charges the base module 18 and optionally an internal battery (not shown) of the base module 18. In this way, the wearable sensor platform 10 may be worn continuously. Thus, in various embodiments, the locations and/or functions of the modules and other components may be changed.

Figure 3:
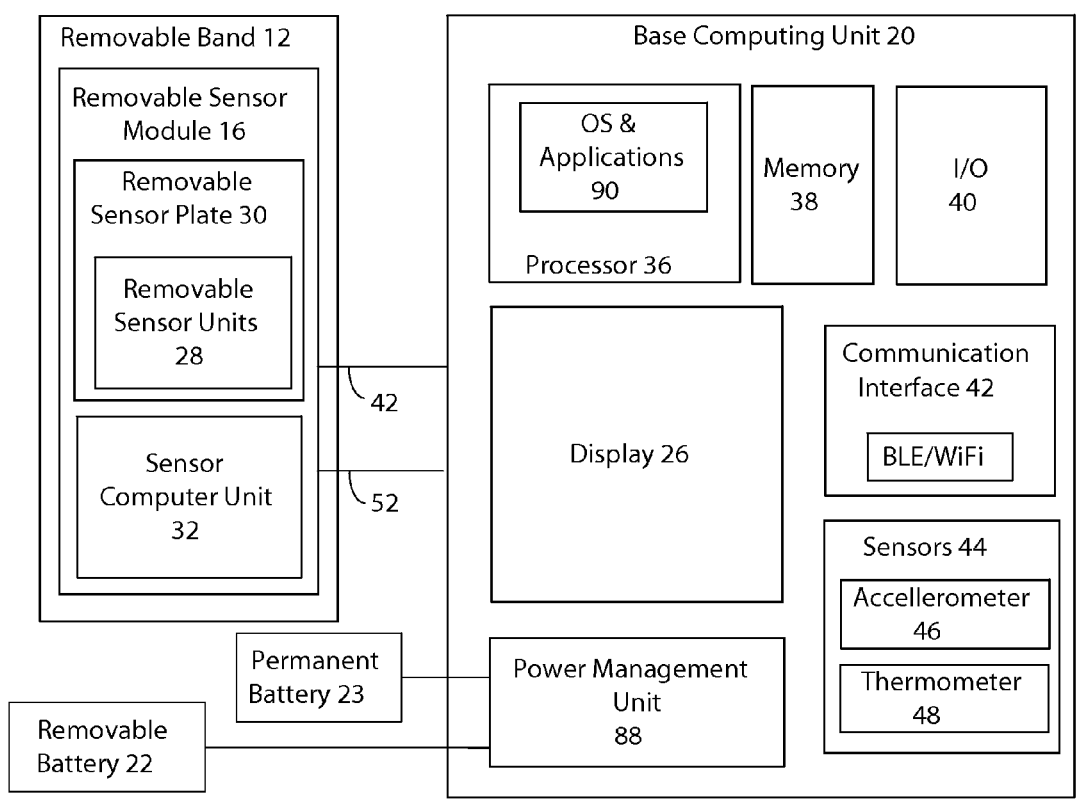
FIG. 3 is a diagram illustrating one embodiment of the modular sensor platform and components comprising the base module.

FIG. 3 is a diagram illustrating one embodiment of the modular sensor platform and components comprising the base module. In this embodiment, the modular sensor platform 10 may include a removable band 12, and a removable sensor module 16 attached to removable band 12. The removable sensor module 16 may further include a removable sensor plate 30 attached to the removable band 12, and removable sensor units 28 attached to the removable sensor plate 30. The removable sensor module 16 may also include a sensor computer unit 32.

The modular sensor platform 10 further comprises a base computing unit 20, a removable battery 22 and a permanent battery 23. In one embodiment, the base computing unit 20 may communicate with the sensor computer 32 through a communication interface 42. In one embodiment, the communications interface 205 may comprise a serial interface.

The base computing unit 20 may include a processor 36, a memory 38, input/output (I/O) 40, a display 26, a communication interface 42, sensors 44, and a power management unit 88.

The processor 36, the memory 38, the I/O 40, the communication interface 42 and the sensors 44 may be coupled together via a system bus (not shown). The processor 36 may include a single processor having one or more cores, or multiple processors having one or more cores. The processor 36 may execute an operating system (OS) and various applications 90. Examples of the OS may include, but not limited to, Linux and Android™, Tizen OS.

The memory 38 may comprise one or more memories comprising different memory types, including DRAM, SRAM, ROM, cache, virtual memory and flash memory, for example. The I/O 40 may comprise a collection of components that input information and output information. Example components comprising the I/O 40 include a microphone and speaker. The communication interface 42 may include a wireless network interface controller (or similar component) for wireless communication over a network. In one embodiment, example types of wireless communication may include Bluetooth Low Energy (BLE) and WLAN (wireless local area network). However, in another embodiment, example types of wireless communication may include a WAN (Wide Area Network) interface, or a cellular network such as 3G, 4G or LTE (Long Term Evolution). In the embodiment shown in FIG. 3, the memory 38 is external to the processor 36. In other embodiments, the memory 38 can be an internal memory embedded in the processor 36.

In one embodiment, the display 26 may be integrated with the base computing unit 20, while in another embodiment, the display 26 may be external from the base computing unit 20. The sensors 44 may include any type of microelectromechanical systems (MEMs) sensor, such as an accelerometer/gyroscope 46 and a thermometer 48, for instance.

The power management unit 88 may be coupled to the removable battery 22 and the permanent battery 23 and may comprise a microcontroller that governs power functions of the base computing unit 20. In one embodiment, the power management unit 88 may also control the supply of battery power to the removable sensor module 16 via power interface 52.

The communication interface 42 may include components for supporting one-way or two-way wireless communications and may include a wireless network interface controller (or similar component) for wireless communication over a network in some implementations, a wired interface in other implementations, or multiple interfaces. In one embodiment, the communication interface 42 is for primarily receiving data remotely, including streaming data, which is displayed and updated on the display 26. However, in an alternative embodiment, besides transmitting data, the communication interface 42 could also support voice transmission. In an exemplary embodiment, the communication interface 42 supports low and intermediate power radio frequency (RF) communications. In certain implementations, example types of wireless communication may include Bluetooth Low Energy (BLE), WLAN (wireless local area network), WiMAX, passive radio-frequency identification (RFID), network adapters and modems. However, in another embodiment, example types of wireless communication may include a WAN (Wide Area Network) interface, Wi-Fi, WPAN, multi-hop networks, or a cellular network such as 3G, 4G, 5G or LTE (Long Term Evolution). Other wireless options may include ultra-wide band (UWB) and infrared, for example. The communication interface 42 may also include other types of communications devices (not shown) besides wireless, such as serial communications via contacts and/or USB communications. For example, a micro USB-type USB, flash drive, or other wired connection may be used with the communication interface 42.

In one embodiment, the display 26 may be integrated with the base computing unit 20; while in another embodiment, the display 26 may be external from the base computing unit 20. Display 26 may be flat or curved, e.g., curved to the approximate curvature of the body part on which the wearable sensor module platform 10 is located (e.g., a wrist, an ankle, a head, etc.).

Display 26 may be a touch screen or gesture controlled. The display 26 may be an OLED (Organic Light Emitting Diode) display, TFT LCD (Thin-Film-Transistor Liquid Crystal Display), or other appropriate display technology. The display 26 may be active-matrix. An example display 26 may be an AMOLED display or SLCD. The display may be 3D or flexible. The sensors 44 may include any type of microelectromechanical systems (MEMs) sensor. Such sensors may include an accelerometer/gyroscope 46 and a thermometer 48, for instance.

The power management unit 88 may be coupled to the power source 22 and may comprise a microcontroller that communicates and/or controls power functions of at least the base computing unit 20. Power management unit 88 communicates with the processor 36 and coordinates power management. In some embodiments, the power management unit 88 determines if a power level falls below a certain threshold level. In other embodiments, the power management unit 88 determines if an amount of time has elapsed for secondary charging.

The power source 22 may be a permanent or removable battery, fuel cell or photo voltage cell, etc. The battery 22 may be disposable. In one embodiment, the power source 22 may comprise a rechargeable, lithium ion battery or the like may be used, for example. The power management unit 88 may include a voltage controller and a charging controller for recharging the battery 22. In some implementations, one or more solar cells may be used as a power source 22. The power source 22 may also be powered or charged by AC/DC power supply. The power source 22 may charge by non-contact or contact charging. In one embodiment, the power management unit 88 may also communicate and/or control the supply of battery power to the removable sensor module 16 via power interface 52. In some embodiments, the battery 22 is embedded in the base computing unit 20. In other embodiments, the battery 22 is external to the base computing unit 20.

Other wearable device configurations may also be used. For example, the wearable sensor module platform can be implemented as a leg or arm band, a chest band, a wristwatch, an article of clothing worn by the user such as a snug fitting shirt, or any other physical device or collection of devices worn by the user that is sufficient to ensure that the sensor units 28 are in contact with approximate positions on the user's skin to obtain accurate and reliable data.

Figure 4:
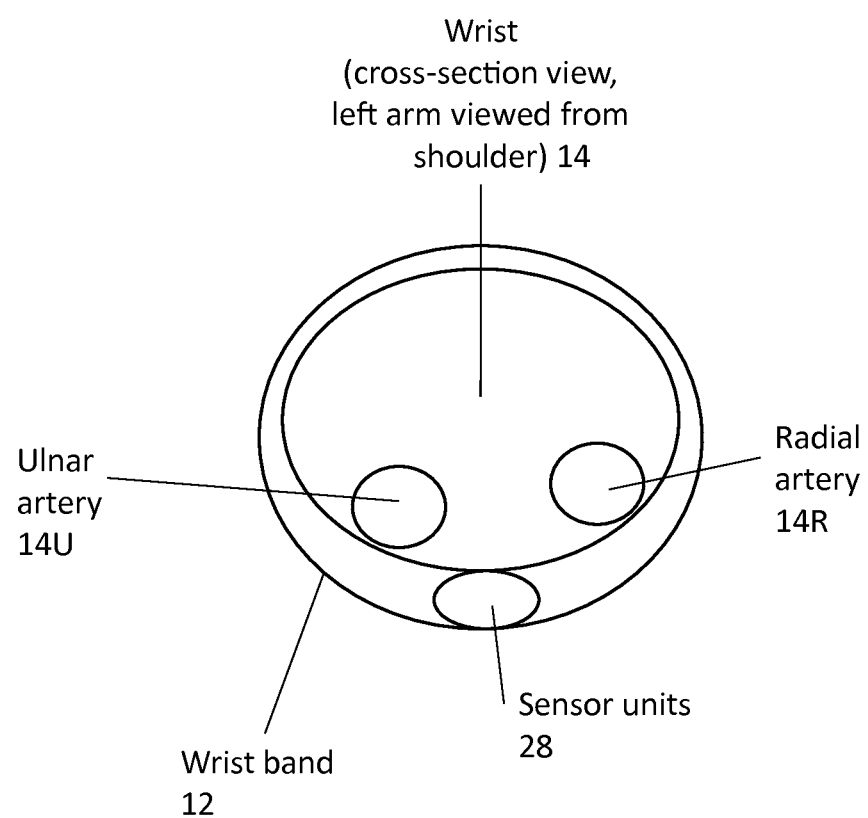
FIG. 4 is a cross-sectional illustration of the wrist with a band mounted sensor in contact for an embodiment used about the wrist.
Figure 5:
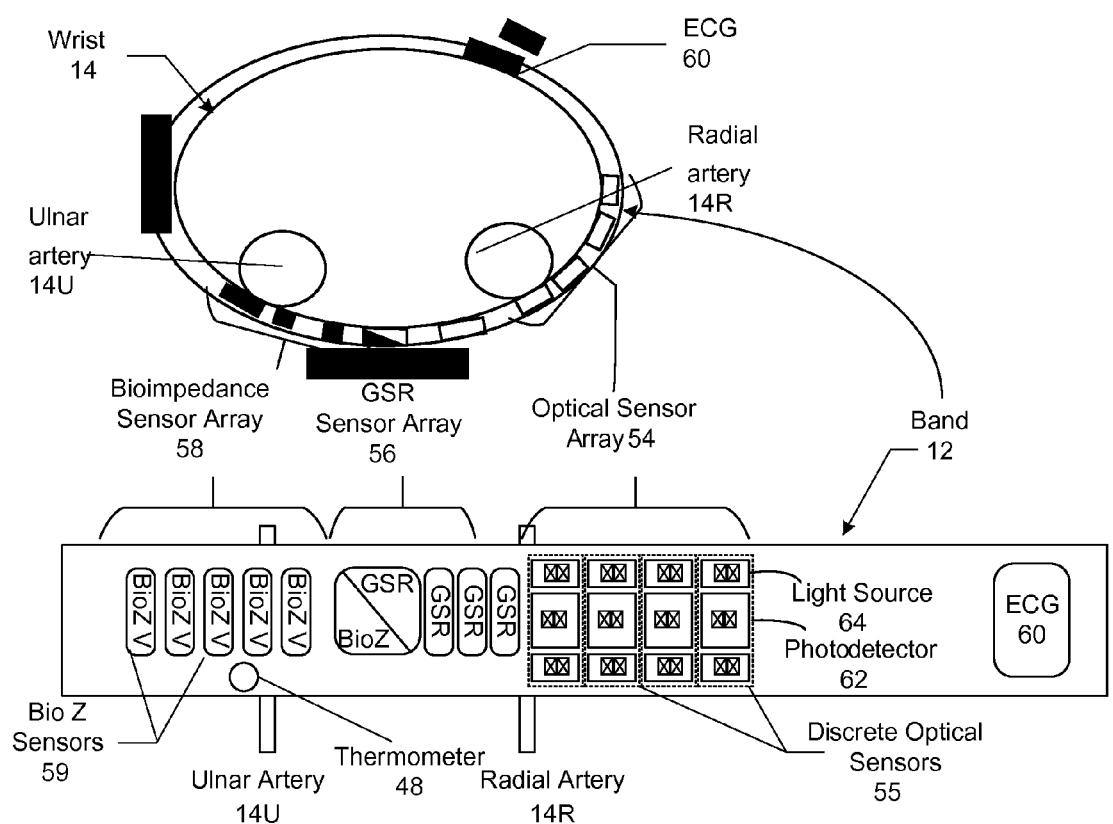
FIG. 5 is a diagram illustrating another embodiment of a modular sensor platform with a self-aligning sensor array system in relation to use about the wrist.

FIG. 4 is a diagram of a cross section of a wrist 14. More specifically, by way of example, FIG. 5 is a diagram illustrating an implementation of a wearable sensor module 10. The top portion of FIG. 5 illustrates the wearable sensor module 10 wrapped around a cross-section of a user's wrist 14, while the bottom portion of FIG. 5 shows the band 12 in an flattened position.

According to this embodiment, the wearable sensor module 10 includes at least an optical sensor array 54, and may also include optional sensors, such as a galvanic skin response (GSR) sensor array 56, a bioimpedance (BioZ) sensor array 58, and an electrocardiogram (ECG) sensor 60, or any combination of which may comprise a sensor array.

According to another embodiment, the sensor units 28 configured as a sensor array(s) comprising an array of discrete sensors that are arranged or laid out on the band 12, such that when the band 12 is worn on a body part, each sensor array may straddle or otherwise address a particular blood vessel (i.e., a vein, artery, or capillary), or an area with higher electrical response irrespective of the blood vessel.

More particularly, as can be seen in FIGS. 4 and 5, the sensor array may be laid out substantially perpendicular to a longitudinal axis of the blood vessel (e.g., radial artery 14R and/or ulnar artery 14U) and overlaps a width of the blood vessel to obtain an optimum signal. In one embodiment, the band 12 may be worn so that the sensor units 28 comprising the sensor array(s) contact the user's skin, but not so tightly that the band 12 is prevented from any movement over the body part, such as the user's wrist 14, or creates discomfort for the user at sensor contact points.

In another embodiment, the sensor units 28 may comprise an optical sensor array 54 that may comprise a photoplethysmograph (PPG) sensor array that may measures relative blood flow, pulse and/or blood oxygen level. In this embodiment, the optical sensor array 54 may be arranged on sensor module 16 so that the optical sensor array 54 is positioned in sufficient proximity to an artery, such as the radial or ulnar artery, to take adequate measurements with sufficient accuracy and reliability.

Further details of the optical sensor array 54 will now be discussed. In general, configuration and layout of each of a plurality of discrete optical sensors 55 may vary greatly depending on use cases. In one embodiment, the optical sensor array 54 may include an array of discrete optical sensors 55, where each discrete optical sensor 55 is a combination of at least one photodetector 62 and at least two matching light sources 64 located adjacent to the photodetector 62. In one embodiment, each of the discrete optical sensors 55 may be separated from its neighbor on the band 12 by a predetermined distance of approximately 0.5 to 2 mm.

In one embodiment, the light sources 64 may each comprise a light emitting diode (LED), where LEDs in each of the discrete optical sensors emit light of a different wavelength. In this regard, the wavelengths of some of the LED's are greater than the wavelengths of other LED's. Example light colors emitted by the LEDs may include green, red, near infrared, and infrared wavelengths. Each of the photodetectors 62 convert received light energy into an electrical signal. In one embodiment, the signals may comprise reflective photoplethysmograph signals. In another embodiment, the signals may comprise transmittance photoplethysmograph signals. In one embodiment, the photodetectors 62 may comprise phototransistors. In alternative embodiment, the photodetectors 62 may comprise charge-coupled devices (CCD).

Figure 6:
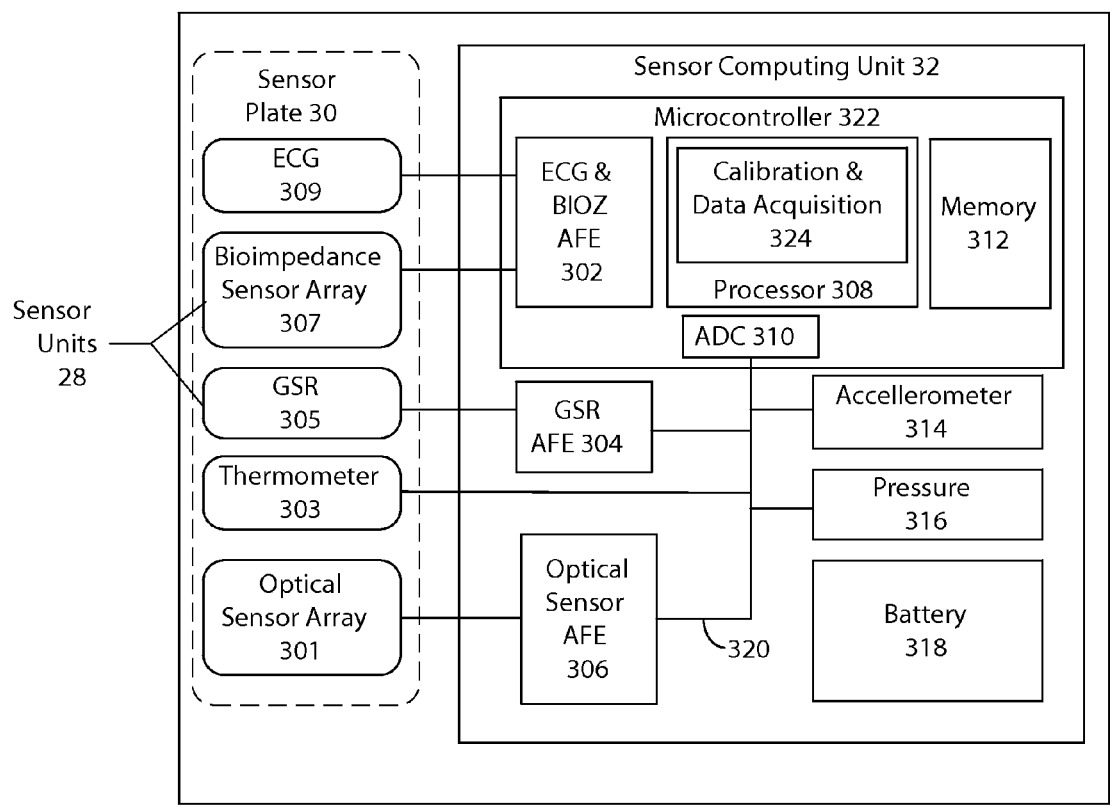
FIG. 6 is a block diagram illustrating components of the sensor module.

FIG. 6 is a block diagram illustrating components of the sensor module. As described above, the sensor module 16 may comprise a plurality of sensor units 28 affixed to a sensor plate 30, and a sensor computing unit 32.

According to one exemplary embodiment, the sensor units 28 may include an optical sensor array 301, a thermometer 303, a galvanic skin response (GSR) sensor array 305, a bioimpedance (BioZ) sensor array 307, and an electrocardiography sensor (ECG) sensor 309, or any combination thereof.

In one embodiment, the optical sensor array 301 may comprise a photoplethysmograph (PPG) sensor array that may measures relative blood flow, pulse and/or blood oxygen level. In one embodiment, the optical sensor array 301 may include an array of discrete optical sensors, where each discrete optical sensor is a combination of at least one photodetector and at least two matching light sources (e.g., LEDs) located adjacent to the photodetector. In this embodiment, the optical sensor array 301 may be arranged on the band so that the optical sensor array 301 straddles a blood vessel, such as the Radial artery or the ulnar artery.

The thermometer 48 may measure temperature or a temperature gradient. The galvanic skin response (GSR) sensor array 305 may comprise two or more GSR sensors that may measure electrical conductance of the skin that varies with moisture level. The bioimpedance (BioZ) sensor array 307 may comprise two or more bioimpedance sensors that measure bioelectrical impedance or opposition to a flow of electric current through the tissue. In the embodiment shown, the bioimpedance sensor array 307 may be arranged or positioned on the band to straddle a blood vessel, such as the Radial or Ulnar artery. In one embodiment, one or more electrodes comprising the bioimpedance sensors may be multiplexed with one or more of the GSR sensors 305. The electrocardiography sensors (ECG) sensor 309 may measure electrical activity of the user's heart over a period of time.

In one embodiment, the ECG 309, the bioimpedance sensor array 307, the GSR 305, the thermometer 303, and the optical sensor array 301 may be coupled to the sensor computing unit 32 that controls and receives data from the sensor units 28. In one embodiment, the sensor computing unit 32 may be part of the band 12 (not shown). In another embodiment, the sensor computing unit 32 may be part of the sensor plate 30.

The sensor computing unit 32 may comprise an ECG and bioimpedance (BIOZ) analog front end (AFE) 302, a GSR AFE 304, an optical sensor AFE 306, a processor 308, and analog-to-digital converter (ADC) 310, a memory 312, a three-axis accelerometer 314, a pressure sensor 316 and a battery 318.

As used herein, an AFE may comprise an analog signal conditioning circuitry interface between corresponding sensors and the ADC 310 or the processor 308. The ECG and BIOZ AFE 302 exchange signals with the ECG 309 and the bioimpedance sensor array 307. The GSR AFE 304 may exchange signals with the GSR sensor array 305. And the optical sensor AFE 306 may exchange signals with the optical sensor array 301. In one embodiment, the GSR AFE 304, the optical sensor AFE 306, the accelerometer 314, and the pressure sensor 316 may be coupled to the ADC 310 via bus 320. The ADC 310 may convert a physical quantity, such as voltage, to a digital number representing amplitude.

In one embodiment, the ECG and BIOZ AFE 302, memory 312, the processor 308 and the ADC 310 may comprise components of a microcontroller 322. The processor 308 in one embodiment may comprise a reduced instruction set computer (RISC), such as a Cortex 32-bit RISC ARM processor core by ARM Holdings, for example.

According to the exemplary embodiment, the processor 308 may execute a calibration and data acquisition component 324 that may perform sensor calibration and data acquisition functions. In one embodiment, the sensor calibration function may comprise a process for self-aligning one or more sensor arrays to a blood vessel. In one embodiment, the sensor calibration may be performed at startup, prior to receiving data from the sensors, or at periodic intervals during operation. In one embodiment, during operation the sensor computing unit 32 may collect and store the sensor data in memory 312 for subsequent transfer to the base computing unit 20.

Figure 7:
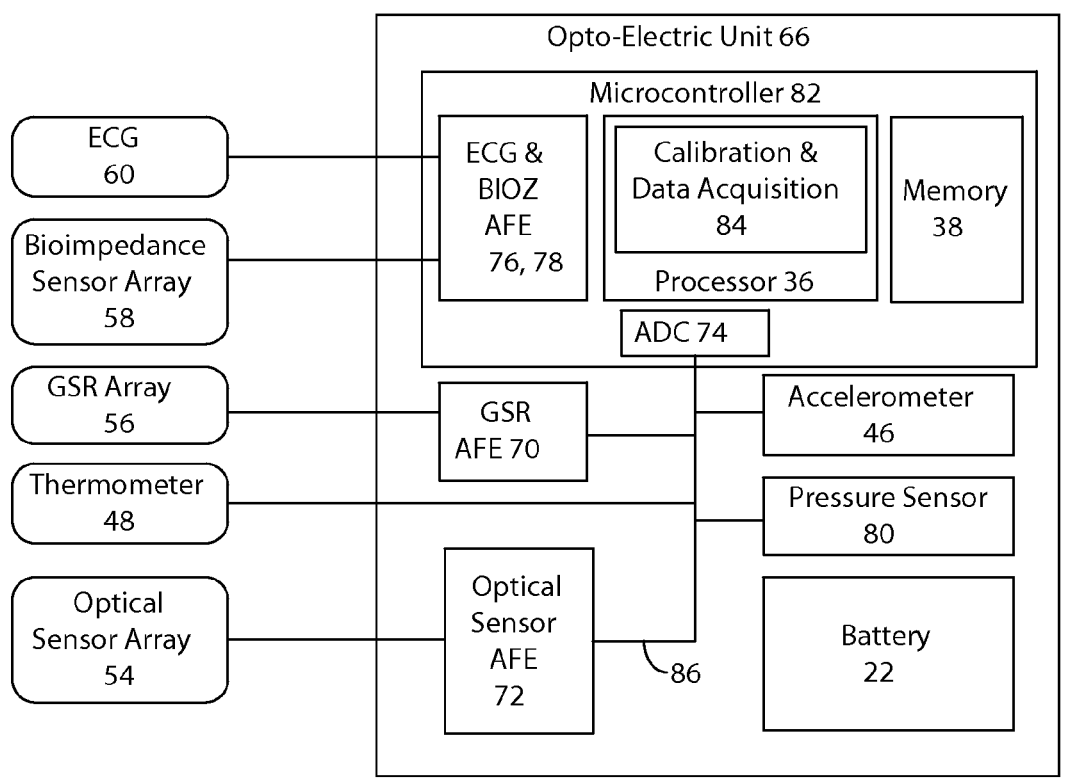
FIG. 7 illustrates another embodiment of a modular wearable sensor platform showing an interior surface.

FIG. 7 is a block diagram illustrating another configuration for components of wearable sensor module in a further implementation. In this implementation, the ECG 60, the bioimpedance sensor array 58, the GSR array 56, the thermometer 48, and the optical sensor array 54 may be coupled to an optical-electric unit 66 that controls and receives data from the sensors on the band 12. In another implementation, the optical-electric unit 66 may be part of the band 12. In an alternative implementation, the optical-electric unit 66 may be separate from the band 12.

The optical-electric unit 66 may comprise an ECG and bioimpedance (BIOZ) analog front end (AFE) 76, 78, a GSR AFE 70, an optical sensor AFE 72, a processor 36, an analog-to-digital converter (ADC) 74, a memory 38, an accelerometer 46, a pressure sensor 80 and a power source 22.

In one embodiment, the ECG and BIOZ AFE 76, 78, memory 38, the processor 36 and the ADC 74 may comprise components of a microcontroller 82. In one embodiment, the GSR AFE 70 and the optical sensor AFE 72 may also be part of the microcontroller 82. The processor 36 in one embodiment may comprise a reduced instruction set computer (RISC), such as a Cortex 32-bit RISC ARM processor core by ARM Holdings, for example. In the embodiment shown in FIG. 7, the memory 38 is an internal memory embedded in the microcontroller 82. In other embodiments, the memory 38 can be external to the microcontroller 82.

According to an exemplary embodiment, the processor 36 may execute a calibration and data acquisition component 84 that may perform sensor calibration and data acquisition functions. In one embodiment, the sensor calibration function may comprise a process for self-aligning one or more sensor arrays to a blood vessel. In one embodiment, the sensor calibration may be performed at startup, prior to receiving data from the sensors, or at periodic intervals during operation.

In another embodiment, the sensor units 28 may also comprise a galvanic skin response (GSR) sensor array 56, which may comprise four or more GSR sensors that may measure electrical conductance of the skin that varies with moisture level. Conventionally, two GSR sensors are necessary to measure resistance along the skin surface. According to one aspect of this embodiment, the GSR sensor array 56 is shown including four GSR sensors, where any two of the four may be selected for use. In one embodiment, the GSR sensors 56 may be spaced on the band 2 to 5 mm apart.

In another embodiment, the sensor units 28 may also comprise bioimpedance (BioZ) sensor array 58, which may comprise four or more BioZ sensors 58 that measure bioelectrical impedance or opposition to a flow of electric current through the tissue. Conventionally, only two sets of electrodes are needed to measure bioimpedance, one set for the "I" current and the other set for the "V" voltage. However, according to an exemplary embodiment, a bioimpedance sensor array 58 may be provided that includes at least four to six bioimpedance sensors 58, where any four of electrodes may be selected for "I" current pair and the "V" voltage pair. The selection could be made using a multiplexor. In the embodiment shown, the bioimpedance sensor array 58 is shown straddling an artery, such as the Radial or Ulnar artery. In one embodiment, the BioZ sensors 58 may be spaced on the band 5 to 13 mm apart. In one embodiment, one or more electrodes comprising the BioZ sensors 58 may be multiplexed with one or more of the GSR sensors 56.

In yet another embodiment, the band 12 may include one or more electrocardiogram (ECG) sensors 60 that measure electrical activity of the user's heart over a period of time. In addition, the band 12 may also comprise a thermometer 48 for measuring temperature or a temperature gradient.

According to an exemplary embodiment of an adjustable sensor support structure, a series of sensors supported by flexible bridge structures may be serially connected edge-to-edge along a band. Such a band with bridge supported sensors may be worn, for example, about the wrist 14. When worn about a measurement site such as the wrist 14, the varying topology of the wrist 14 may cause force(s) to simultaneously be exerted upon the bridges due to compliance of the band to the varying topology of the wrist 14.

Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other. Various cloud-based platforms and/or other database platforms may be employed in certain implementations of the modular sensor platform 10 to, for example, receive and send data to the modular sensor platform 10. One such implementation is architecture for multi-modal interactions (not shown). Such architecture can be employed as a layer of artificial intelligence between wearable devices, like modular sensor platform 10, and the larger cloud of other devices, websites, online services, and apps. Such an architecture also may serve to translate (for example by monitoring and comparing) data from the modular sensor platform 10 with archived data, which may be then used to alert, for example, the user or healthcare professional about changes in condition. This architecture further may facilitate interaction between the modular sensor platform 10 and other information, such as social media, sports, music, movies, email, text messages, hospitals, prescriptions to name a few.

FIG. 8 illustrates another embodiment of a modular wearable sensor platform or device 800 showing an interior surface 804. The wearable sensor platform 800 is analogous to the wearable sensor platforms 10 and thus includes analogous components having similar labels. In this embodiment, the wearable sensor platform 800 includes an optional smart device or base module 808, a band 812, and an interface 816. In some other embodiments, the wearable sensor platform 800 does not include the optional base module 808. In some embodiments, the modular wearable sensor platform or device 800 is a smart watch or a smart phone.

In the embodiment shown in FIG. 8, the interface 816 includes a sensor plate receptacle 820 for receiving a modular sensing circuitry, discussed hereinafter. In other embodiment, the interface receptacle 816 includes a cavity (not shown) that receives a modular sensing circuitry. In some embodiments, the sensor plate receptacle 820 includes fasteners 824 for keeping or securing a modular sensing circuitry in place. In some embodiments, the fasteners 824 include, but are not limited to, one or more of a magnet, a notch, Velcro, a clip, a screw, pogo pins, contacts, detents, and the like. In some other embodiments, the fasteners 824 include threaded through-holes and receptacles to receive driving fasteners such as screws to secure a modular sensing circuitry in place.

In the embodiment shown in FIG. 8, the fasteners 824 are disposed at either edge of the sensor plate receptacle 820. In other embodiments, the fasteners 824 can be embedded or disposed on a backplate 828 of the sensor plate receptacle 820. In yet other embodiments, the fasteners 824 can be disposed on both the backplate 828 and the edges of the sensor plate receptacle 820. In some other embodiments, the sensor plate receptacle 820 includes a universal-serial-bus (USB)-type receptacle.

FIG. 8A illustrates a second interface receptacle 840 showing an exemplary micro-USB-type interface 844 located on a backplate 848 for receiving a modular sensing circuitry that has a micro-USB-type receptacle. In the embodiment shown in FIG. 8A, the second interface receptacle 840 includes one micro-USB-type interface 844. In other embodiments, the second interface receptacle 840 may include more than one micro-USB-type interface 844. Further, in the embodiment shown in FIG. 8A, the micro-USB-type interface 844 is centrally located. In other embodiments, the micro-USB-type interface 844 can be located in a different portion of the backplate 848.

Referring back to FIG. 8, the sensor plate receptacle 820 may have internal wiring (not shown) embedded or integrated with the band 812, and is in communication with the base module 808 and a coupled modular sensing circuitry. For example, an internal power source (not shown) of the base module 808 can power one or more sensors and/or a processor of the coupled modular sensing circuitry. Conversely, data received or processed by the coupled modular sensing circuitry may be transmitted to the base module 808 via the internal wiring. In some embodiments, however, the communication between the base module 808 and the coupled modular sensing circuitry can be wireless. The wearable sensor platform 800 also includes a clasp 832 for holding the band 812 over a body part, for example, the wrist 14.

In the embodiment shown in FIG. 8, the band 812 has various optional fixed sizes to be wearable over different wrist sizes. For example, the band 812 can have different lengths ranging from about 135 mm for a small wrist to about 210 mm for a large wrist. In other embodiments, the band 812 is an adjustable band to be wearable over different wrist sizes. In still other embodiments, the band 812 includes a plurality of sub-bands (not shown) for circulation of air in and around the wrist, thereby provides additional comfort. Further, the band 812 generally consists of chemically inert material, medical-grade material, hypoallergenic silicone, rubber, Graphene, and the like. In some embodiments, the band 812 has a textured interior surface to minimize slipping.

FIG. 9 illustrates a sensor module or modular sensing circuitry 900 that can be coupled to the modular wearable sensor platform 800 of FIG. 8. The modular sensing circuitry 900 includes a sensor plate 904. The sensor plate 904 includes a plurality of sensors 908, 910, and a sensor computing unit or processor 912 that is similar to the sensor computing unit 32 of FIG. 2. In some embodiments, the sensors 908, 910 include, but are not limited to, an optical sensor array, a thermometer, a galvanic skin response (GSR) sensor array, a bioimpedance (BioZ) sensor array, an electrocardiogram (ECG) sensor, or any combination thereof. The sensors 908 may also include biological sensors (e.g., pulse, pulse oximetry, body temperature, blood pressure, body fat, etc.), proximity detector for detecting the proximity of objects, and environmental sensors (e.g., temperature, humidity, ambient light, pressure, altitude, compass, etc.).

In the embodiment shown in FIG. 9, the sensor module 900 is selectively removable or detachable, and includes an interface 916 that mechanically engages the sensor plate receptacle 820. The interface 916 also includes fasteners (not shown) that secure the modular sensing circuitry 900 to the interface 816 of FIG. 8. In some embodiments, the fasteners (not shown) include, but are not limited to, one or more of a magnet, a notch, Velcro, a clip, a screw, pogo pins, contacts, detents, and the like. In some other embodiments, the fasteners (not shown) include threaded through-holes and receptacles to receive driving fasteners such as screws to secure the modular sensing circuitry 900 to the interface 816 of FIG. 8.

In the embodiment as shown in FIG. 9, both the sensor module 900 and the sensor plate 904 are contoured to conform to the wrist 14 (of FIG. 4). When the device 800 is worn over the wrist 14, the sensor plate 904 may be in contact with the skin of the wrist. In other embodiments, the sensor plate 904 is a flexible plate. When selectively pressed, the sensor plate 904 is pressed against the skin of the wrist 14, thereby contacting the skin of the wrist 14. It should be understood that the present invention is not limited to usage with the wrist. It should also be understood that, in addition to the sensor plate 904 being replaceable and removable, each of the individual sensors 908, 910 can also be replaceable and removable. For example, each of the sensors 908, 910 can be snapped in place into the sensor plate 904, and thus is in communication with the processor 912 with wiring integrated in the sensor plate 904. In this way, only a sensor 908, 910 that needs replacement or repaired is replaced.

Figure 10:
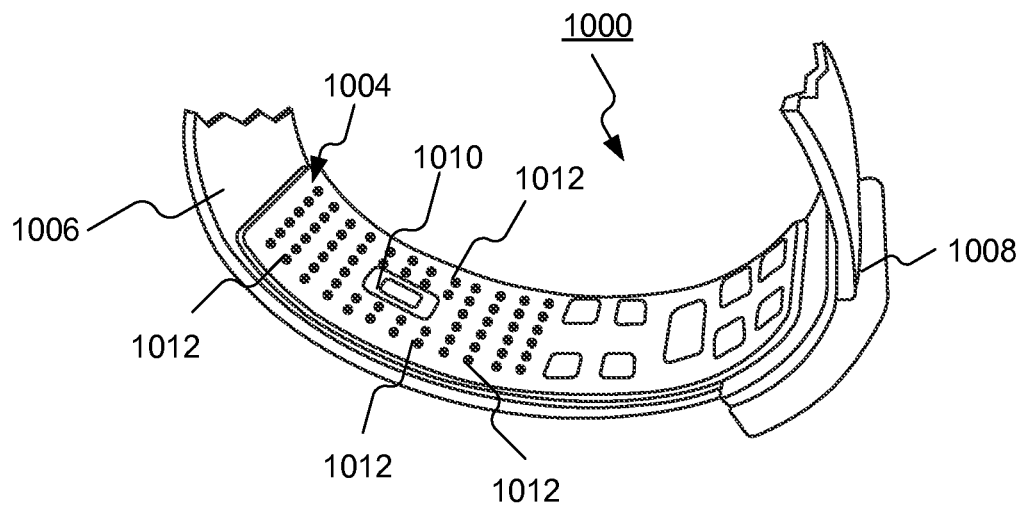
FIG. 10 illustrates another exemplary modular sensing circuitry in accordance with embodiments of the present invention.

FIG. 10 illustrates an exemplary complementary metal-oxide-semiconductor ("CMOS") sensor module 1000 in accordance with embodiments of the present invention. The CMOS sensor module 1000, like the sensor module 900, can also be removably and interchangeably engaged to the platform 800 at the interface 816. That is, the CMOS sensor module 1000 also includes an interface (not shown) similar to the interface 916 of FIG. 9. Similarly, the CMOS sensor module 1000 may also include fasteners similar to the fasteners as discussed with respect to FIG. 9. In this regard, a user can remove the modular sensing circuitry 900 of FIG. 9, and replace the modular sensing circuitry 900 of FIG. 9 with the CMOS sensor module 1000, for example, for different types of physiological activity measurement.

The CMOS sensor module 1000 includes an optical sensor array 1004, for example, a photoplethysmogram (PPG) sensor array that may measure relative blood flow, pulse and/or blood oxygen level. In the embodiment shown, the CMOS sensor module 1000 is engaged with an interface (not shown) similar to the interface 816 of FIG. 8 on a band 1006 with a clasp 1008. The optical sensor array 1004 includes a plurality of image sensors 1010 packaged near to each other, and a plurality of light sources 1012. In some embodiments, the light sources 1012 include multi-spectral light-emitting diodes (LED's). In other embodiments, the light sources 1012 may include multi-spectral laser sources.

In some embodiments, the image sensors 1010 are positioned in sufficient proximity to an artery, such as the radial or ulnar artery, of the wrist 14 of FIG. 4 to take adequate measurements with sufficient accuracy and reliability. In the embodiment shown in FIG. 10, the image sensors 1010 are centrally located with respect to the light sources 1012. In the embodiment shown, the light sources 1012 are arranged or distributed uniformly in a regular rectangular array. In other embodiments, the light sources 1012 can be distributed in a predefined pattern. For example, the light sources 1012 can be laid out around the image sensors 1010 in a circular array with the image sensors 1010 as the center. For another example, the light sources 1012 can be laid out asymmetrically with respect to the image sensors 1010. In such embodiments, the image sensors 1010 can be placed near only one side of the image sensors 1010.

In the embodiment shown in FIG. 10, the light sources 1012 include LEDs of four different colors. However, in other embodiments, there may be two, three, or many more colors of LEDs in the optical sensor array 1004. In some embodiments, some of the light sources 1012 may be chosen with the same central wavelength but have different spectral bandwidths. In one embodiment, layout of the colors of the multi-spectral light sources 1012 in the optical sensor array 1004 may be regular. In other embodiments, some colors of the multi-spectral light sources 1012 may be represented in the optical sensor array 1004 more often than other colors of the light sources 1012.

In some embodiments, the light sources 1012 could be electrically controlled to be lit simultaneously. In some embodiments, each of the light sources 1012 in the optical sensor array 1004 is individually addressable. For example, the brightness and/or duration of each of the light sources 1012 in the optical sensor array 1004 can be individually controlled. In the embodiment shown in FIG. 10, each of the image sensors 1010 has a resolution of 200×200 pixels. In other embodiments, the image sensors 1010 can have various or adjustable sizes and resolutions depending on application, and/or depending on the size of the wrist 14, or the length of the band 1006.

In the embodiment shown in FIG. 10, color filters (not shown) can be used in conjunction with the image sensors 1010 to specifically detect a predefined wavelength of a signal. In other embodiments, the image sensors 1010 do not include any additional color filter to detect all wavelengths. In still other embodiments, some of the image sensors 1010 are equipped with color filters, while other image sensors 1010 are not equipped with color filters. For example, filters (not shown) can be placed on some of the image sensors 1010 while the rest of the image sensors 1010 do not include any color filter. In this regard, a user can specifically tune the optical sensor array 1004 to detect a predefined set of physiological activity.

In some embodiments, the filters can be placed in a plurality of large bands creating pixel bands on the image sensors 1010. The pixel bands can be broadly chosen to match red, green, blue, and infrared (IR). In other embodiments, the color filters can be chosen to match one or more specific spectral bandwidths of the light sources 1012 chosen in the optical sensor array 1004. In still other embodiments, the filters chosen do not need to be uniform among the image sensors 1010. For example, each of the image sensors 1010 can have a different set of color filters. In other embodiments, other configurations of filters can be used. In some embodiments, color filters can be differentiated down to the pixel level if that is desired. In some embodiments, optical films (not shown) can be added to different sections of the image sensors 1010 to make them more or less sensitive to the direction of photons received. It should be understood that, in some embodiments, the sensor plate 1004 also includes other sensors similar to the sensors 908, 910 of FIG. 9, and a sensor computing unit similar to the sensor computing unit 912 of FIG. 9. For example, the sensor plate 1004 can also include a thermometer, a galvanic skin response (GSR) sensor array, a bioimpedance (BioZ) sensor array, an electrocardiogram (ECG) sensor, biological sensors (e.g., pulse, pulse oximetry, body temperature, blood pressure, body fat, etc.), proximity detector for detecting the proximity of objects, and environmental sensors (e.g., temperature, humidity, ambient light, pressure, altitude, compass, etc.).

Figure 11:
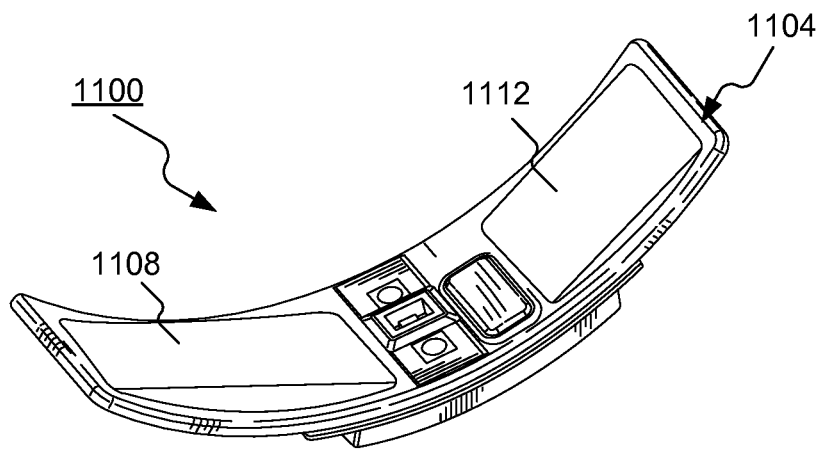
FIG. 11 illustrates an operational flow chart of a sensing process for measuring data of a predefined area in accordance with embodiments of the present invention.

FIG. 11 shows another sensor module or modular sensing circuitry 1100 that can be coupled to the modular wearable sensor platform 800 of FIG. 8. The modular sensing circuitry 900 includes a sensor plate 1104. Unlike the modular sensing circuitry 900 of FIG. 9, the sensor plate 1104 includes a plurality of large sensors 1108 and 1112. In this regard, the large sensors 1108, 1112 can be uncomfortable to wear for an extended period of time. In this regard, each of the large sensors 1108 and 1112 may be subdivided into a plurality of smaller sensor segments. In some embodiments, for example, when a sensor, such as, for example, the sensor 1108 is considered as too large for conforming to the contour of a body part, for example, the wrist 14, a sensor 1108 is segmented into a plurality of sensor segments. For example, when a bioimpedance sensor is configured to detect the bioimpedance of the wrist, but is considered large when compared to the contour of the wrist 14, the bioimpedance sensor is subdivided into two or more bioimpedance sensor segments that are better shaped to contour the wrist.

In this regard, when the sensor 1108 is configured to measure data, such as, for example, a physiological activity, at a predefined surface area, the sensor 1108 may be subdivided into a plurality of sensor segments (not shown) to effectively measure the same physiological activity. In some embodiments, the sensor segments have the same total sensing surface areas, or the sum of all individual sensing surface areas generally matches the predefined surface area. For example, the total of all individual sensing surface areas is the same as the predefined surface area. For another example, data measured with the sum of all individual sensing surface areas effectively equals the data that would have been measured with the predefined sensing surface area. In still other embodiments, the sensor segments have different sensing surface areas, but data measured with the sum of all individual sensing surface areas still effectively matches data that would have been measured with the predefined sensing surface area.

Figure 12:
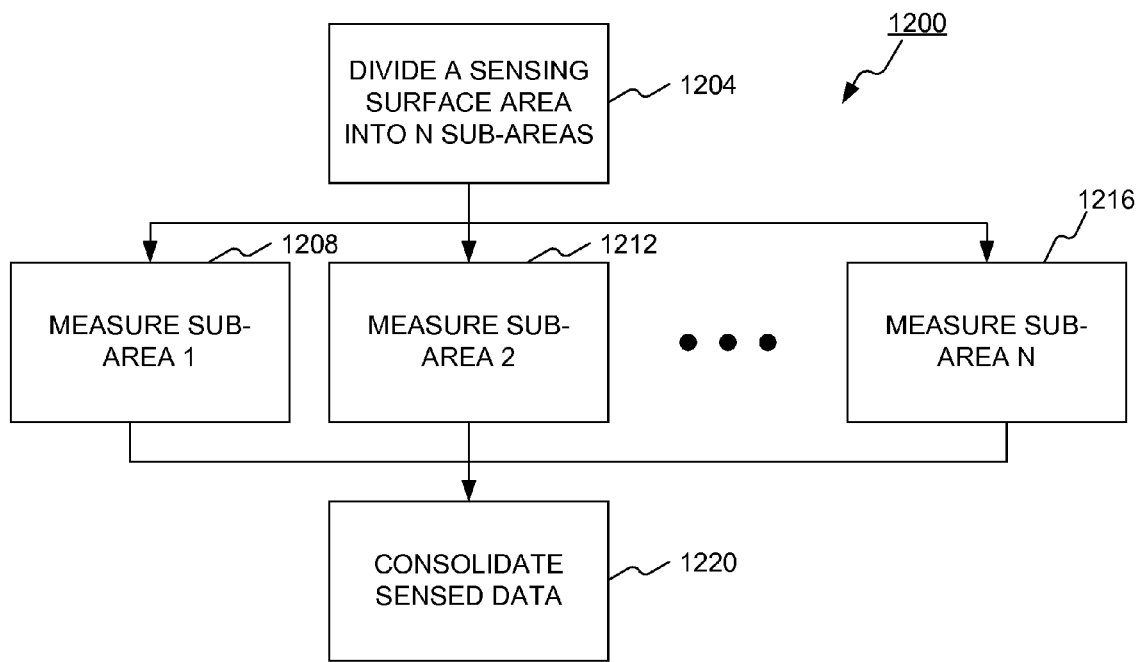
FIG. 12 illustrates an operational flow chart of a measurement process for measuring data indicative of blood pressure of an individual in accordance with embodiments of the present invention.

FIG. 12 illustrates an operational flow chart of a sensing process 1200 for measuring data of a predefined area in accordance with embodiments of the present invention. At step 1204, the sensing process 1200 divides the predefined area into a plurality of sub-areas. In the embodiment shown in FIG. 12, there are N sub-areas. At steps 1208, 1212, 1216, the sensing process 1200 measures or senses data at each of the sub-areas for a portion of a physiological activity. In some embodiments, the measurements at steps 1208, 1212, 1216 are carried out simultaneously. In other embodiments, the measurements at steps 1208, 1212, 1216 are carried out in a timed manner. For example, step 1208 is followed by step 1212, which is followed by step 1216. The data measured at each of the sub-areas are consolidated and combined to form the desired set of data of the physiological activity at step 1220.

Figure 13:
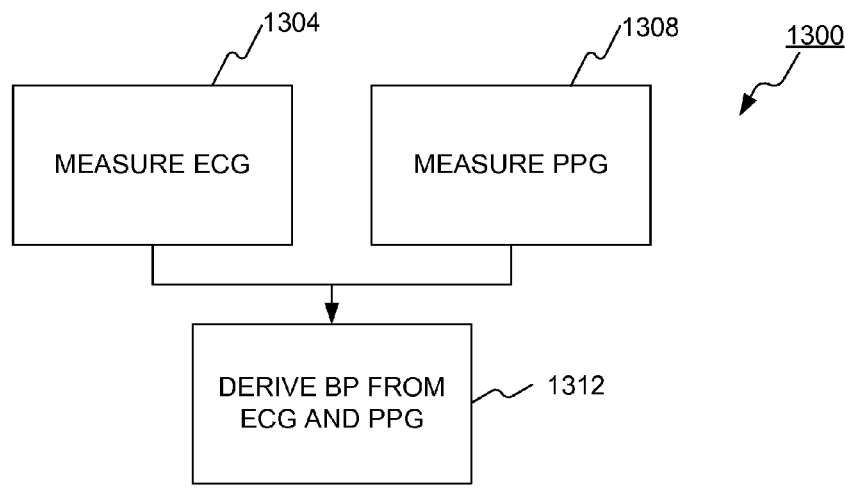
FIG. 13 illustrates an operational flow chart of a measurement process for measuring data indicative of blood pressure of an individual.

FIG. 13 illustrates an operational flow chart of a measurement process 1300 for measuring data indicative of blood pressure of an individual in accordance with embodiments of the present invention. At step 1304, a modular wearable sensor platform similar to the modular wearable sensor platform 1000 measures an electrocardiogram (ECG) with one or more sensors (similar to the sensors 908, 910 of FIG. 9) disposed on a band similar to the band 812 of FIG. 8. At step 1208, the modular wearable sensor platform similar to the modular wearable sensor platform 1000 measures a photoplethysmogram (PPG) with sensors similar to the image sensors 1010 of FIG. 10. At step 1312, a sensor computing unit similar to the sensor computing unit 912 of the FIG. 9 then derives and processes data indicative of the blood pressure of a user from the ECG and the PPG. In some embodiments, at step 1312, a processor similar to the processor 912 of FIG. 9 can determine a timing difference between a heart electrical impulse and an actual blood flow passing through the artery. Based on the difference determined, the processor similar to the processor 912 of FIG. 9 can estimate a pulse arrival time (PAT), and thus can calculate a blood pressure.

Blood pressure is correlated with the pulse transition time (PTT) which may be calculated from the PAT. In one embodiment, calibration may be necessary both to calculate the PTT as well as to determine the blood pressure. In some embodiments, both the systolic and diastolic blood pressure may be determined. One problem with correlated blood pressure calculations lies in changes in the relationship of the signals. When ECG is measured, different lead lengths or different positioning of the leads on the body will change the absolute timing in comparison with a PPG sensor. In addition, because these signals are often measured using different devices, the timing difference between the two devices is determined and/or calibrated along with other physiological parameters. Furthermore, timing jitter between the two signals on different devices may require longer averaging of signals to measure a steady signal; this can impede measurements of fast blood pressure variability. In some embodiments, sensors can be placed on a modular band similar to the band 812 of FIG. 8. In such embodiments, when positioning of the sensors is consistent, and measurements of both the PPG and ECG will have consistent timing. Because both ECG sensors similar to the ECG sensors of FIG. 10 and PPG sensors similar to the optical sensor array 1004 are placed on the same platform similar to the modular sensor platform 10, 800, timing changes or jitters due to wiring with the modular sensor platform 10, 800 will be reduced, minimized, or eliminated in some embodiments. In other embodiments, other types of sensors could be used in place of PPG sensors to measure blood flow or pulse arrival at the sensors. For example, in one embodiment, a bioimpedance sensor could be used. In other embodiments, data from both a PPG sensor and a bioimpedance sensor could be placed on the same platform similar to the modular sensor platform 10, 800 to improve data quality for calculating the pulse arrival and thus produce a more accurate and precise blood pressure reading.

The present invention has been described in accordance with the embodiments shown, and there could be variations to the embodiments, and any variations would be within the spirit and scope of the present invention. For example, the exemplary embodiment can be implemented using hardware, software, a computer readable medium containing program instructions, or a combination thereof. Software written according to the present invention is to be either stored in some form of computer-readable medium such as a memory, a hard disk, or a CD/DVD-ROM and is to be executed by a processor.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

Additionally, In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

We claim:

1. A device for measuring data indicative of a physiological activity of a user and being wearable on a body part of the user, the device comprising:
a band having an interior surface and a receptacle on the interior surface of the band; and
a sensor module, having an interface being removably and interchangeably insertable into the receptacle via the interior surface, and being configurable to be in contact with the body part, wherein the sensor module includes:
a modular sensing circuitry; and
a plurality of light sources disposed on the interior surface adjacent the modular sensing circuitry, the light sources being configured to emit lights onto the body part, the modular sensing circuitry configured to receive data indicative of a photoplethysmogram (PPG) signal of the user.

2. A device of claim 1, wherein the light sources have different spectral wavelengths.

3. A device of claim 2, wherein the wavelength of one of the light sources is greater than the wavelength of another of the light sources.

4. A device of claim 1, wherein the light sources have different spectral bandwidths.

5. A device of claim 1, wherein the light sources are uniformly distributed with respect to the modular sensing circuitry.

6. A device of claim 1, wherein the light sources are configured to be lit simultaneously.

7. A device of claim 1, wherein the light sources are configured to be individually addressable.

8. A device of claim 1, wherein brightness and duration of the light sources are configured to be individually addressable.

9. A device of claim 1, wherein the light sources include one or more lasers.

10. A device of claim 1, wherein the modular sensing circuitry further includes a color filter configured to measure a predefined wavelength of a signal.

11. A device of claim 1, wherein the modular sensing circuitry further includes a plurality of sensors configured to measure data indicative of one or more of the physiological activities.

12. A device of claim 11, wherein the sensors have different sensor sizes.

13. A device of claim 1, wherein the modular sensing circuitry is replaceable with a different type of modular sensing circuitry.

14. A device of claim 1, wherein the modular sensing circuitry comprises any combination of optical sensor array, a thermometer, a galvanic skin response (GSR) sensor array, a bioimpedance (BioZ) sensor array, and an electrocardiography sensor (ECG) sensor.

15. A device of claim 14, wherein the optical sensor array includes an array of discrete optical sensors, where each discrete optical sensor is a combination of at least one image sensor and at least two matching light sources located adjacent to the image sensor.

16. A device of claim 14, wherein the optical sensor array is arranged on the band so that the optical sensor array straddles a blood vessel.

17. A device of claim 14, wherein the bioimpedance (BioZ) sensor array is arranged on the band to straddle a blood vessel.

18. A device of claim 1, wherein the modular sensing circuitry further includes a sensor and a sensor computing unit coupled to the sensor.

19. A device of claim 18, wherein the sensor computing unit further comprises an ECG and bioimpedance (BIOZ) analog front end (AFE), a GSR AFE, an optical sensor AFE, a processor, and analog-to-digital converter (ADC), a memory 312, a three-axis accelerometer, a pressure sensor and a battery.

20. A device of claim 19, wherein the processor executes a calibration and data acquisition component that performs sensor calibration and data acquisition functions.

21. A device of claim 20, further comprising a base module, wherein the base module further includes a base computing unit that includes a processor, a memory, a communication interface and a set of sensors including an accelerometer and thermometer.

22. A device of claim 21, wherein the band is integrated with the base module.

23. A device for measuring data indicative of a physiological activity of a user and being wearable on a body part of the user, the device comprising:
 a band having an interior surface and a receptacle on the interior surface of the band; and
 a sensor module, having an interface being removably and interchangeably insertable into the receptacle via the interior surface, and being configurable to be in contact with a surface area of the body part, wherein the sensor module includes:
 a modular sensing circuitry; and
 a plurality of light sources, being subdivided into a plurality of segments, each of the segments having a number of the light sources, the segments having a total surface area matching the surface area, the light sources being disposed on the interior surface adjacent the modular sensing circuitry, the light sources being configured to emit lights onto the body part, the modular sensing circuitry configured to receive data indicative of a photoplethysmogram (PPG) signal of the user.

* * * * *